US006171301B1

(12) United States Patent
Nelson et al.

(10) Patent No.: US 6,171,301 B1
(45) Date of Patent: Jan. 9, 2001

(54) APPARATUS AND METHOD FOR DYNAMIC COOLING OF BIOLOGICAL TISSUES FOR THERMAL MEDIATED SURGERY

(75) Inventors: J. Stuart Nelson; Thomas E. Milner, both of Irvine, CA (US); Lars O. Svaasand, Trondheim (NO)

(73) Assignee: The Regents of the University of California, Oakland, CA (US)

( * ) Notice: Under 35 U.S.C. 154(b), the term of this patent shall be extended for 0 days.

(21) Appl. No.: 08/963,531

(22) Filed: Nov. 3, 1997

Related U.S. Application Data

(62) Division of application No. 08/441,930, filed on May 15, 1995, now Pat. No. 5,814,040.

(51) Int. Cl.[7] ...................................................... A61N 5/06
(52) U.S. Cl. ................................ 606/9; 606/10; 606/20
(58) Field of Search ................................. 606/2, 3, 9–13, 606/20–24; 607/88, 89

(56) References Cited

U.S. PATENT DOCUMENTS

| 5,057,104 | * | 10/1991 | Chess .................................. 606/9 |
| 5,344,418 | * | 9/1994 | Ghaffari ............................. 606/9 |
| 5,810,801 | * | 9/1998 | Anderson et al. ............... 606/9 |
| 5,820,626 | * | 10/1998 | Baumgardner ................. 606/13 |

OTHER PUBLICATIONS

Nelson et al, "Dynamic Epidermal Cooling . . . Stain", Arch. Dermatol., vol. 131, pp. 695–700, 1995.*
Anvari et al, "Selective Cooling . . . Procedures", Phys. Med. Biol., vol. 40, pp. 241–252, 1995.*

* cited by examiner

Primary Examiner—Michael Peffley
(74) Attorney, Agent, or Firm—Daniel L. Dawes

(57) ABSTRACT

Dynamically cooling the epidermis of a port wine stain patient undergoing laser therapy permits maximization of the thermal damage to the port wine stain while at the same time minimizing nonspecific injury to the normal overlying epidermis. A cryogenic spurt is applied to the skin surface for a predetermined short period of time in the order of tens of milliseconds so that the cooling remains localized in epidermis while leaving the temperature of deeper port wine stain vessels substantially unchanged. The result is that epidermal denaturation and necrosis which normally occurs in uncooled laser irradiated skin sites does not occur and that clinically significant blanching of the port wine stains at the dynamically cooled sites establishes that selective laser photothermolysis of the port wine stain blood vessels is achieved. In addition, dynamic epidermal cooling reduces patient discomfort normally associated with flashlamp-pumped pulsed dye laser therapy.

24 Claims, 5 Drawing Sheets

APPARATUS AND METHOD FOR DYNAMIC COOLING OF BIOLOGICAL TISSUES FOR THERMAL MEDIATED SURGERY

This application is a division of application Ser. No. 08/441,930 filed May 15, 1995 which application is now U.S. Pat. No. 5,814,040.

This invention was made with Government support under Grant No. 1R03RR6988-01 awarded by the National Institute of Health. The Government has certain rights in this invention

BACKGROUND OF THE INVENTION

1. Field of the Invention

The invention relates to the field of laser surgery, and in particular, to the thermal treatment of biological tissues with laser pulses.

2. Description of the Prior Art

The illustrated embodiment of the invention is described below in the context of treatment of port wine stain birthmarks in human skin, although the scope of the invention is much broader in that it applies to all types of thermal surgeries. A port wine stain is congenital, progressive, vascular malformation of the dermis involving capillaries and possibly perivenular nerves. Port wine stains occur in approximately three percent of one thousand live births. Although port wine stains may be found anywhere on the body, they mostly appear on the face and are noted over the dermatome distribution of the first and second trigeminal nerves.

In early childhood, port wine stains are faint pink macules, but the lesions tend to darken progressively to red-purple and by middle age, often become raised as a result of the development of vascular papules or nodules and occasionally tumors. The hypertrophy of underlying bone and soft tissue occurs in approximately two-thirds of the patients with port wine stain, and serves to further disfigure the facial features of many children.

The prior art treatments for port wine stain includes scalpel surgery, ionizing radiation, skin grafting, dermabrasion, cryosurgery, tattooing and electrotherapy. Clinical results have been considered unsatisfactory due to the cosmetically unacceptable scarring post treatment. All of these prior art techniques are no longer considered viable treatment options for this reason.

A flashlamp-pumped pulsed dye laser offers a superior approach and therapy due to its ability to selectively destroy cutaneous blood vessels. Light passing through the epidermis is preferentially absorbed by hemoglobin which is the major chromophore in blood in the ectatic capillaries in the upper dermis. The radiant energy is converted to heat causing thermal damage and thrombosis in the targeted vessels. Prior art studies have shown that the flashlamp-pumped pulsed dye laser produce good results in the vast majority of pediatric and adult patients.

Histopathological studies of port wine stains show a normal epidermis overlying an abnormal plexus of dilated blood vessels located on a layer in the upper dermis as diagrammatically depicted in cross sectional view in FIG. 1. The predominate endogenous cutaneous chromophores, absorbing light at the 585 nanometer wavelength produced by flashlamp-pumped pulsed dye laser, are melanin and hemoglobin. Therefore, the overlying epidermal pigment layer comprises a barrier or an optical shield through which the light must first pass to reach the underlying port wine stain blood vessels. The absorption of laser energy by melanin causes localized heating in the epidermis and reduces the light dosage reaching the blood vessels, thereby decreasing the amount of heat produced in the targeted port wine stains and leading to suboptimal blanching of the lesion.

The ratio of heat generated in port wine stains to that of the epidermis is a measure of the relative heating of the port wine stain relative to the epidermis. The best clinical results realized in a port wine stain patient undergoing laser therapy are obtained when the patient's ratio of heat generated in the port wine stain to that in the epidermis is greater than or equal to one. Unfortunately, for many lesions, the threshold for epidermal damage following laser therapy is very close to the threshold for permanent blanching of the port wine stain.

One prior art method which has been tried is the application of ice cubes to the skin surface prior to laser treatment, B. A. Gilchrest et al., "*Chilling Port Wine Stains Improves the Response to Argon Laser Therapy,*" Plast. Reconstr. Surg. 1982; 69:278–83. However, these treatments have not proven entirely satisfactory, nor more importantly led to an improved therapeutic response, that is improved blanching of the port wine stain.

Other prior art attempts to provide surface cooling of the epidermis using plastic bags filled with ice placed on the skin surface for five minutes, compressed freon gas used during irradiation, or chilled water spread directly on the area being irradiated have also been explored, A. J. Welch et al., "*Evaluation of Cooling Techniques for the Protection of the Epidermis During ND-YAG Laser Irradiation of the Skin,*" Neodymium-YAG Laser in Medicine, Stephen N. Joffe editor 1983. However, these studies were done with pig cadaver tissue and normally utilized cooling periods of 2 to 14 seconds. The reported results with freon were good in only 28.5 percent of the cases, in some cases, the skin surface was momentarily frozen, and in others, the freon jet was found to overcool the skin surface.

Therefore, what is needed is some type of methodology or apparatus which can be effectively used to uniformly provide positive results, namely allowing treatment of deeper or selected layers of tissue without nonspecific damage to the upper or nonselected layers.

BRIEF SUMMARY OF THE INVENTION

The invention is a method for using dynamic cooling to perform photothermolysis of selected buried chromospheres in biological tissues. The method comprises the steps of cooling a selected portion of the biological tissue to establish a predetermined dynamic temperature profile, and irradiating the first portion and a second portion of the biological tissue to thermally treat the second portion of the biological tissue while leaving the first portion of the biological tissue substantially undamaged. As a result, the second portion of the biological tissue may be laser treated without damage to the first portion.

The first portion of the tissue lies adjacent the second portion and the step of irradiating the second portion comprises the step of irradiating the second portion of the biological tissue through the first portion.

In the illustrated embodiment the biological tissue is skin. The first portion is epidermis and the second portion is dermis lying beneath melanin contained in the epidermis. The step of establishing a predetermined dynamic temperature profile establishes a dynamically cooled profile substantially only in the epidermis.

The step of establishing a predetermined dynamic temperature profile is performed by providing a cryogenic spurt to the biological tissue at a site which is later irradiated. The cryogenic spurt is comprised of cryogenic droplets or a mist.

The method can be characterized as establishing a thermal heat sink thermally coupled to the first portion of the biological tissue. The step of establishing a thermal heat sink comprises the step of eliminating an air-to-surface insulating barrier at the first portion of the biological tissue.

The step of providing the cryogenic spurt to the first portion of the biological tissue comprises the step of disposing a liquid at a predetermined cooled temperature onto the surface of the first portion of the biological tissue. The liquid has a boiling point below normal temperatures of the first portion of the biological tissue and the cryogenic spurt has a time duration sufficient to provide approximately a 40–50 degree Centigrade temperature drop at the surface of the first portion of the biological tissue. The duration of the cryogenic spurt is of the order of tens of milliseconds.

The method may further comprise the step of reestablishing a predetermined dynamic temperature profile in the first portion of the biological tissue after irradiation of the second portion of the biological tissue. The step of reestablishing the predetermined dynamic temperature profile in the first portion of the biological tissue is performed immediately after both the first and second portions of the biological tissue are irradiated by applying more cyrogen to the first portion immediately after the last treatment.

The invention is also an apparatus for laser treatment of biological tissue comprising a pulsed laser, and a controllable element for providing a spurt of a cooling substance to an irradiation site on the biological tissue. A timing control triggers the pulsed laser and the controllable element for triggering the pulsed laser to fire a predetermined laser pulse after the controllable element provides the spurt of cooling substance. As a result, the irradiation site of the biological tissue is dynamically cooled to selectively allow laser treatment of tissue portions of the irradiation site. In the illustrated embodiment the pulsed laser is a flashlamp-pumped pulsed dye laser. The controllable element comprises a cryogenic reservoir and an electronically controlled solenoid valve coupled to the cryogenic reservoir for adiabatically releasing a spurt of the cryogen over a preselected time period. The timing control comprises a digital delay generator. The time duration of the spurt of cooling substance is determined by a triggering delay generated by the digital delay generator coupled to the controllable element and to the pulsed laser.

Still more specifically the invention is a method of laser treating port wine stain birthmarks in human skin having an epidermis containing melanin and a dermis containing the port wine stains. The method comprises the steps of dynamically cooling the epidermis such that onset of a predetermined temperature profile within the epidermis is achieved within a time period substantially shorter than the thermal diffusion time between the port wine stain in the dermis and the overlying epidermis. The port wine stain in the dermis is irradiated through the epidermis for a time period sufficient to selectively destroy cutaneous blood vessels within the port wine stain. As a result, the port wine stain is destroyed without substantial biological damage to the epidermis.

The invention and its various embodiments may be better visualized by now turning to the following drawings wherein like elements are referenced by like numerals.

BRIEF DESCRIPTION OF THE DRAWINGS

FIG. 6a shows the skin 10 minutes after the laser exposure.

The invention and its various embodiments can now be understood in terms of the following detailed description.

DETAILED DESCRIPTION OF THE PREFERRED EMBODIMENTS

Dynamically cooling the epidermis of a port wine stain patient undergoing laser therapy permits maximization of the thermal damage to the port wine stain while at the same time minimizing nonspecific injury to the normal overlying epidermis. A cryogenic spurt is applied to the skin surface for a predetermined short period of time in the order of tens of milliseconds so that the cooling remains localized in epidermis while leaving the temperature of deeper port wine stain vessels substantially unchanged. The result is that epidermal denaturation and necrosis which normally occurs in uncooled laser irradiated skin sites does not occur and that clinically significant blanching of the port wine stains at the dynamically cooled sites establishes that selective laser photothermolysis of the port wine stain blood vessels is achieved. In addition, dynamic epidermal cooling reduces patient discomfort normally associated with flashlamp-pumped pulsed dye laser therapy.

It is believed that all previously tried methods for cooling laser irradiated sites to prevent epidermal damage have essentially failed due to the thermal response of skin to prolonged cooling in which a near steady state temperature distribution is achieved. In steady state or prolonged cooling, the internal temperature increases linearly from the skin surface down into the subcutaneous layers. Therefore, in addition to cooling the epidermis, prolonged cooling also reduces the ambient temperature of the lower lying port wine stain blood vessels. Any increase in the threshold for epidermal damage achieved by temperature reduction is almost entirely offset by the additional energy required to heat the port wine stain blood vessels to a sufficient temperature to obtain selective laser photothermolysis.

With dynamic cooling according to the invention, the epidermis can be selectively cooled. When a spurt of cryogen is applied to the skin surface for an appropriately short period, that is on the order of tens of milliseconds, the cooling remains localized in the epidermis while leaving the temperature of deeper port wine stain vessels unchanged.

Figure 1:
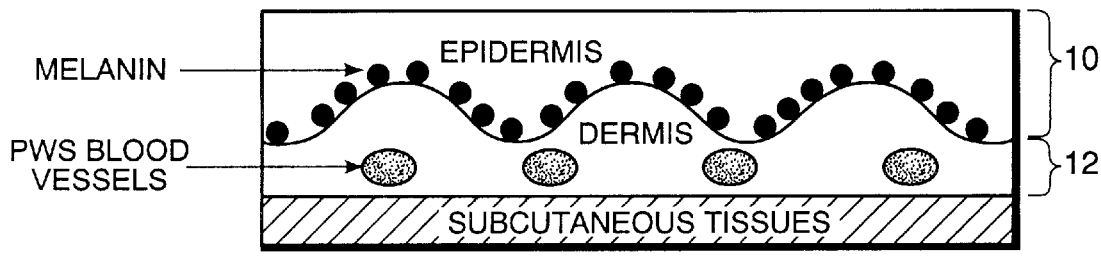
FIG. 1 is a highly diagrammatic side cross sectional view of human skin tissue having a port wine stain embedded in the dermis.
Figure 2:
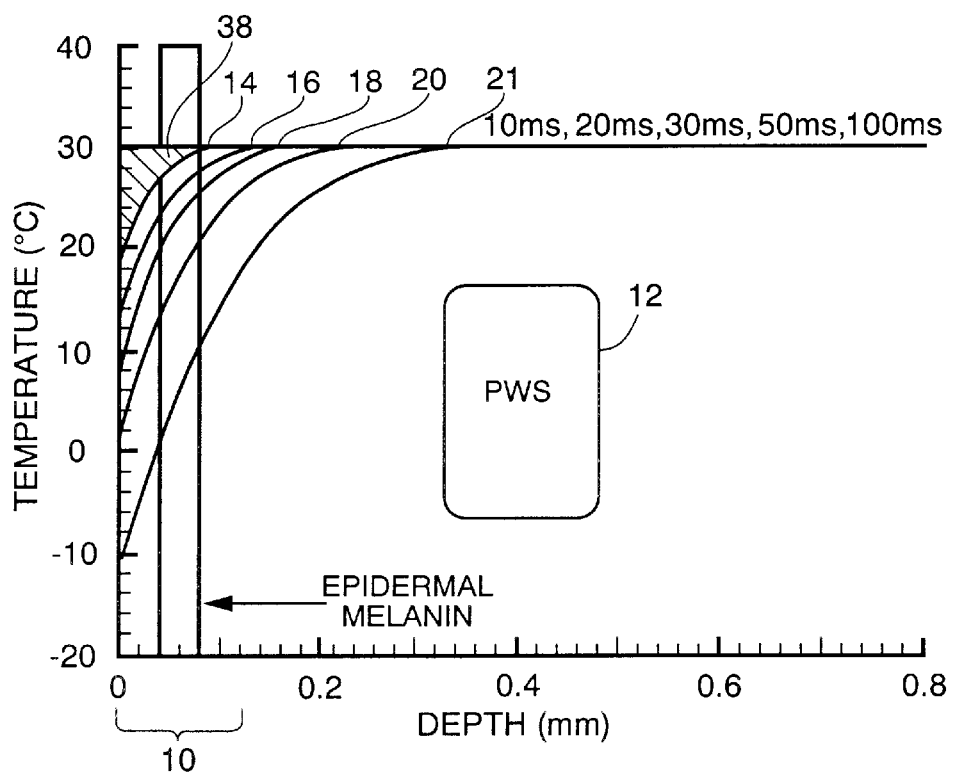
FIG. 2 is a graph illustrating the dynamic cooling temperature profiles and skin as a function of depth corresponding to 10 to 100 millisecond cryogenic spurts.

See, for example, FIG. 2, which is a graph of the dynamic cooling temperature profiles in skin as a function of depth for 10 to 100 microsecond cryogenic spurts. The vertical scale is shown in degrees Centigrade, while the horizontal scale is the depth in the tissue in millimeters.

Region 10 generally represents the position of the epidermal melanin Region 12 diagramatically depicts the typical depth at which port wine stains are found. Curve 14 is the temperature profile immediately after a 10 millisecond cryogenic spurt applied to the test site as described below. Curves 16, 18, 20 and 21 are the temperature profiles for 20, 30, 50 and 100 millisecond cryogenic spurts, respectively. It can be appreciated that for cryogenic spurts of these durations substantially all of the temperature cooling which occurs is in the area of the skin above port wine stain region 12. Meanwhile temperatures in port wine stain region 12 are unchanged.

If the skin is dynamically cooled so that heat is removed at a constant rate, a heat flux $F_0$, the instantaneous skin temperature, $T_s$, is given by the equation (1)

$$T_s(z, t) = T_i + \frac{F_0}{K}\left(2\sqrt{\frac{xt}{\pi}}\ e^{-z^2/4xt} - z\,\text{erfc}\frac{z}{2\sqrt{xt}}\right) \quad (1)$$

Where z is the skin depth, $T_i$ is the initial temperature at the skin surface, K is the thermal conductivity, X is the thermal diffusivity and erfc is the complementary error function. From equation (1), the temperature reduction of the skin surface in response to dynamic cooling can be shown to be:

$$\Delta T_o = T_i - T_s(z = 0, t_c) = \frac{2F_0}{K}(xt_c/\pi)^{1/2} \quad (2)$$

Hence, surface temperature reduction is proportional to the heat flux, $F_0$, and the square root of the cooling time. For a given flux, the exposure time to the cryogenic spurt, $t_c$, must be long enough to produce a large $T_0$, but short enough to avoid conductive cooling of the port wine stain vessels in region 12.

Figure 3:
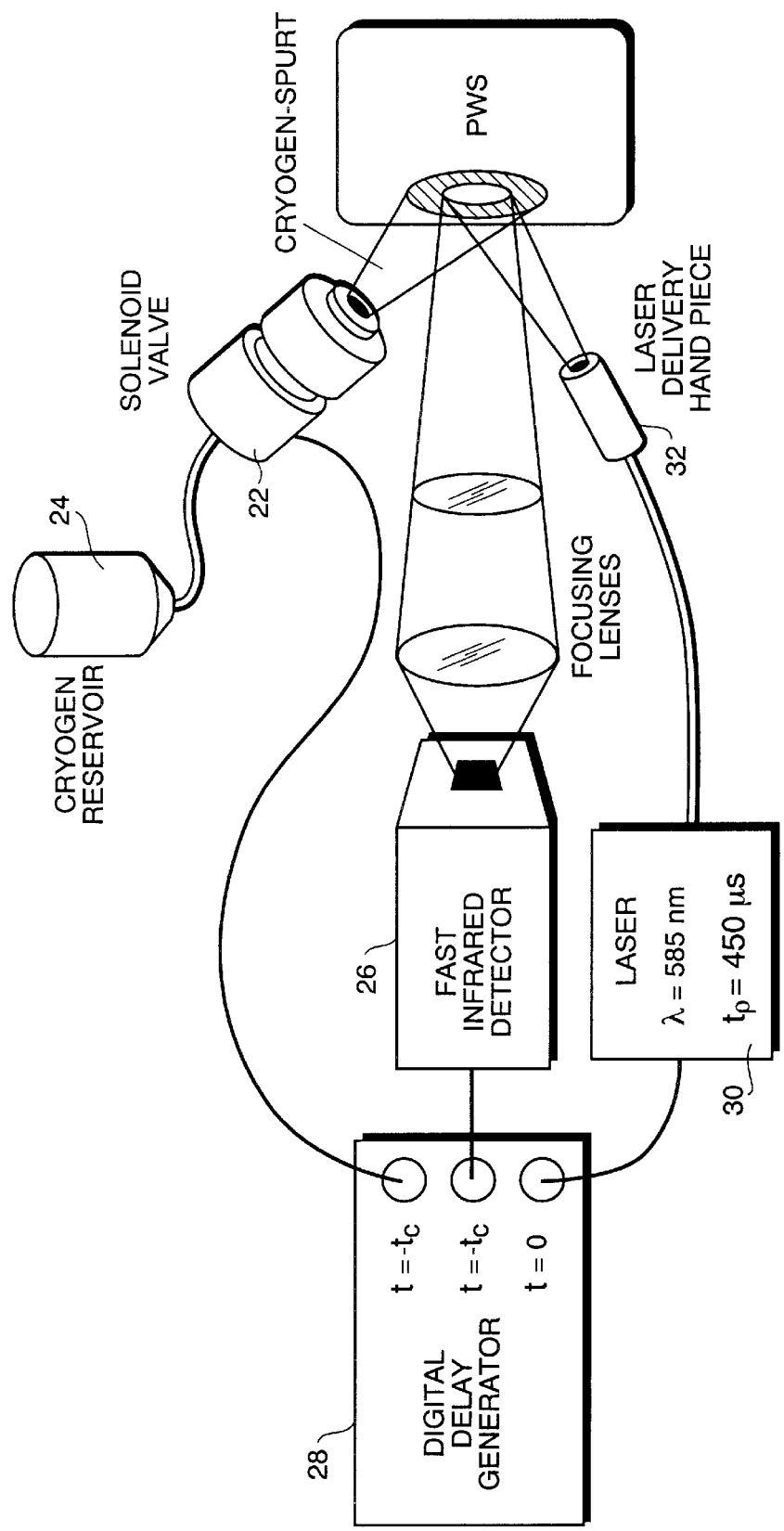
FIG. 3 is a simplified diagram showing use of the apparatus of the invention to conduct the methodology of the invention.

FIG. 3 is a highly diagrammatic depiction of one embodiment of the apparatus of the invention in which the methodology described above is practiced. A test cryogen, which in the illustrated embodiment is tetrafluoroethane, $C_2H_2F_4$ with a boiling point of –26.5 degrees Centigrade, and which is an environmentally compatible, nontoxic, nonflammable freon substitute, is used as a surface cooling agent. Short cryogenic spurts of the order of tens of milliseconds are delivered onto the skin surface through an electronically controlled solenoid valve 22, which valve is supplied with test cryogen from a cryogenic reservoir 24.

A fast infrared detector 26, which in the illustrated embodiment is an InSb 128×128 focal plane array detector, sensitive in the 3–5 micron spectral range, is used to measure the skin surface temperature before, during and after the cryogenic spurt and laser pulse. Detector 26 is used in the system of FIG. 3 as a means of verifying test results. It is to be understood that in a commercial embodiment of the invention, detector 26 may be omitted or a simpler and less expensive thermal detector used in its place.

Detector 26 is triggered by a digital delay circuit 28 as manufactured by Stanford Research Systems of Sunnyvale, Calif. Solenoid valve 22 is similarly triggered at a time of $-T_c$ simultaneously with detector 26. At a time t=0, a flashlamp-pumped pulsed dye laser 30 operating at a wavelength of 585 nanometers with a pulse width of 450 microseconds is triggered.

The exposure time to the cryogenic spurt and the interval between the application of cryogenic spurts and the onset of the laser pulse are controlled by delay generator 28 and are usually less than 1 millisecond. The cryogenic spurt released from solenoid valve 22 is comprised of droplets of cryogen cooled by evaporation and mist formed by adiabatic expansion of vapor. Droplets of cryogen have been found to provide a better heat sink that merely cooled gas. At the test site of the skin surface, the cryogenic spurt is made to cover an approximate circular zone of about 7 millimeters in diameter concentric with the laser spot which is approximately 5 millimeters in diameter. Clearly, the shape, size and disposition of the cooled region relative to the irradiated region can be varied according to the application in many ways consistent with the teachings of the invention.

The following results were obtained with human patients with port wine stains subject to standard screening and consent protocols. Test sites were selected and identified by a skin marker in a manner depicted in the photographs FIG. 6a–c. Eighteen test sites were selected for each patient, six of which were irradiated without cooling and twelve of which were irradiated with dynamic cooling of the invention. The sites were selected on inconspicuous sectors of the port wine stain, for example under the arm, which were generally representative of the entire lesion. The six sites selected for laser exposure with dynamic cooling were irradiated by laser 30 at a maximum light dosage of approximately 10 Joules per square centimeter. The other twelve test sites received identical laser irradiation following a short cryogenic spurt of the order of tens of milliseconds. Untreated areas of the port wine stain served as a control having no light exposure. The test sites were observed over the course of time to determine if any adverse effects occurred and if blanching of the port wine stain subsequently developed. Each of the subjects were evaluated initially to form a base line, and twice a week for four weeks thereafter, and monthly through six months after laser irradiation.

Figure 4:
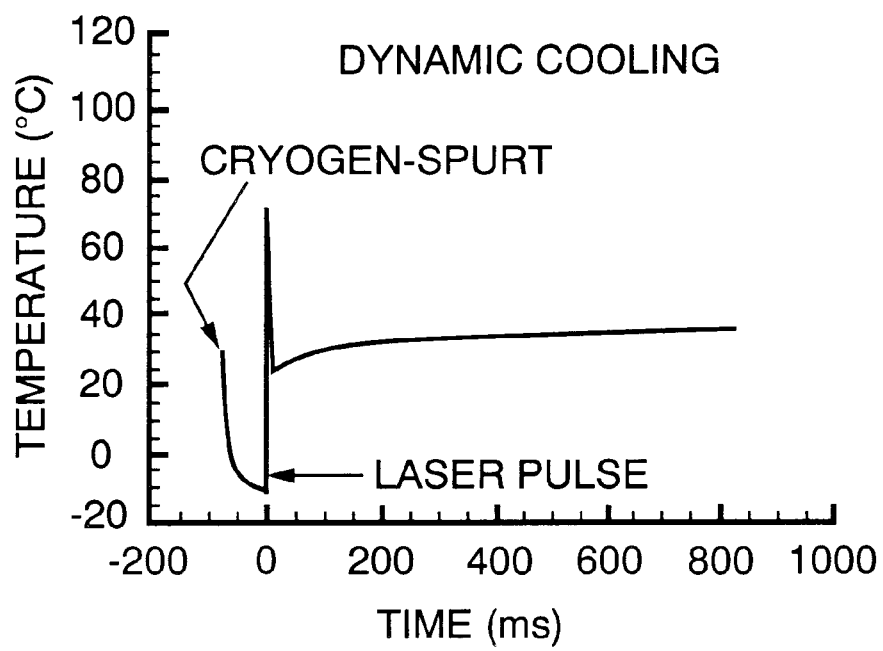
FIG. 4 is an empirical graph of the skin surface temperature measurements obtained using a fast infrared detector from adjacent port wine stain test sites on a human patient which has had the test site dynamically cooled according to the invention.
Figure 5:
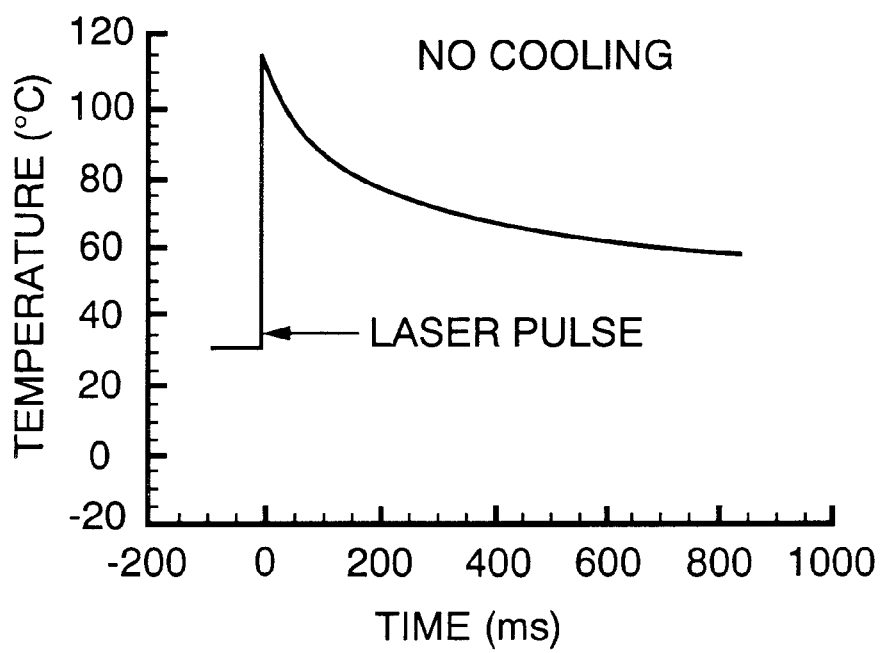
FIG. 5 is a graph of the skin surface temperature measurements obtained as in the case of FIG. 4 from a test site on the same patient in which the test site has had no cooling.

FIGS. 4 and 5 illustrate the skin surface temperature profiles which were measured using infrared detector 26 from one of the patient's port wine stain test sites, namely a test site that was cooled by an 80 millisecond cryogenic spurt as shown in FIG. 4 and an uncooled test site depicted in FIG. 5. The graphs of FIGS. 4 and 5 were typical of all of the patients tested. The vertical scale in FIG. 4 is the skin temperature in degrees Centigrade and time scale is horizontally shown in milliseconds with the laser pulse occurring at time 0.

FIG. 4 shows that the skin surface temperature prior to laser exposure was reduced for the cooled test site by as much as 40 degrees Centigrade. Therefore, the baseline skin surface temperature prior to laser exposure was approximately –10 degrees Centigrade on the cooled site as opposed to 30 degrees on the uncooled site. After a 10 Joule per square centimeter light dosage from the laser, the skin surface temperature, just after time 0, for both the cooled and uncooled port wine stain sites, jumped 80 degrees Centigrade. However, because the baseline skin surface temperature at the cooled site was initially minus 10 degrees Centigrade, the maximum surface temperature achieved immediately after laser exposure was 70 degrees Centigrade at the cooled site as opposed to 110 degrees Centigrade at the uncooled site as shown in FIG. 5.

Infrared images of the uncooled test site taken by detector 26 show a temperature rise immediately after laser exposure with persistent surface heating 90 milliseconds later indicating a slow dissipation of heat trapped near the skin-air interface. Images taken by detector 26 of a cooled site show lower surface temperatures observed immediately after laser exposure and the arrival of a delayed thermal wave at 90 milliseconds after exposure as the heat generated in the port wine stain gradually diffuses from the buried blood vessels toward the cooled skin surface. Thus, the method of the invention also provides a means for measuring the depth and size of the subsurface port wine stain vessels using a fast infrared detector.

Figure 6A:
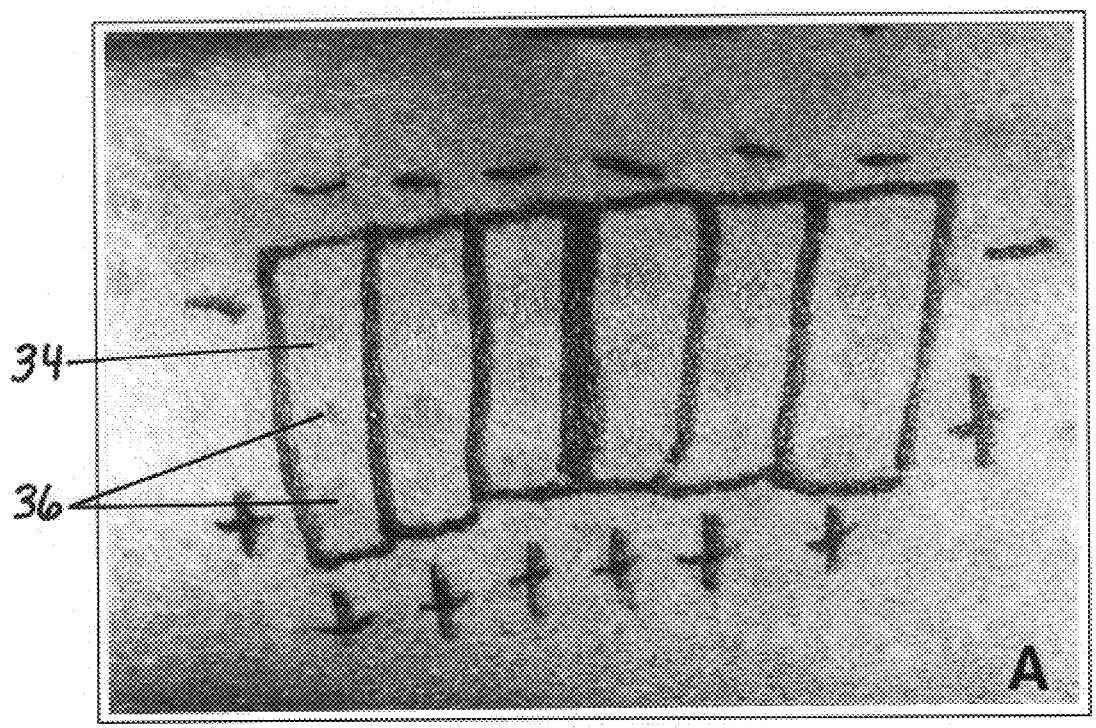
FIG. 6a is a photograph of a port wine stain test site in a human patient having three rows of exposed sites in which the upper row is uncooled and the lower two rows dynamically cooled according to the invention.
Figure 6B:
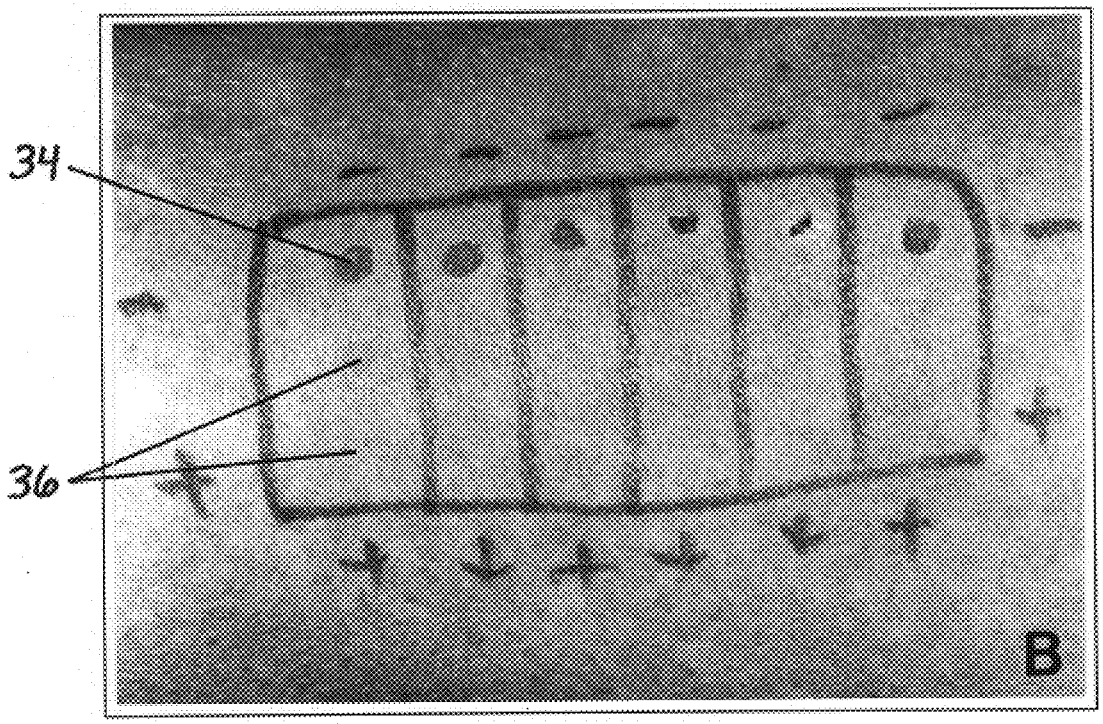
FIG. 6b is a photograph of the test sites of FIG. 6a as seen 10 days after laser exposure.

FIG. 6a which was taken 10 minutes after laser exposure show blistering indicative of thermal injury at the uncooled sites 34 and show in FIG. 6b eschar formation indicative of epidermal denaturation and necrosis 10 days after laser irradiation.

In contrast, no skin surface textural changes are noted at the cooled sites 36 in FIGS. 6a taken 10 minutes after exposure or in FIG. 6b 10 days after exposure. Dynamic epidermal cooling permits exposure of port wine stain skin to an incident light dosage that was expected and subsequently proven to cause epidermal damage at uncooled port wine stain test sites. When the epidermis was rapidly cooled from ambient skin temperature at about 30 degrees Centigrade to minus 10 degrees Centigrade, immediately prior to laser exposure, no epidermal injury is noted.

Figure 6C:
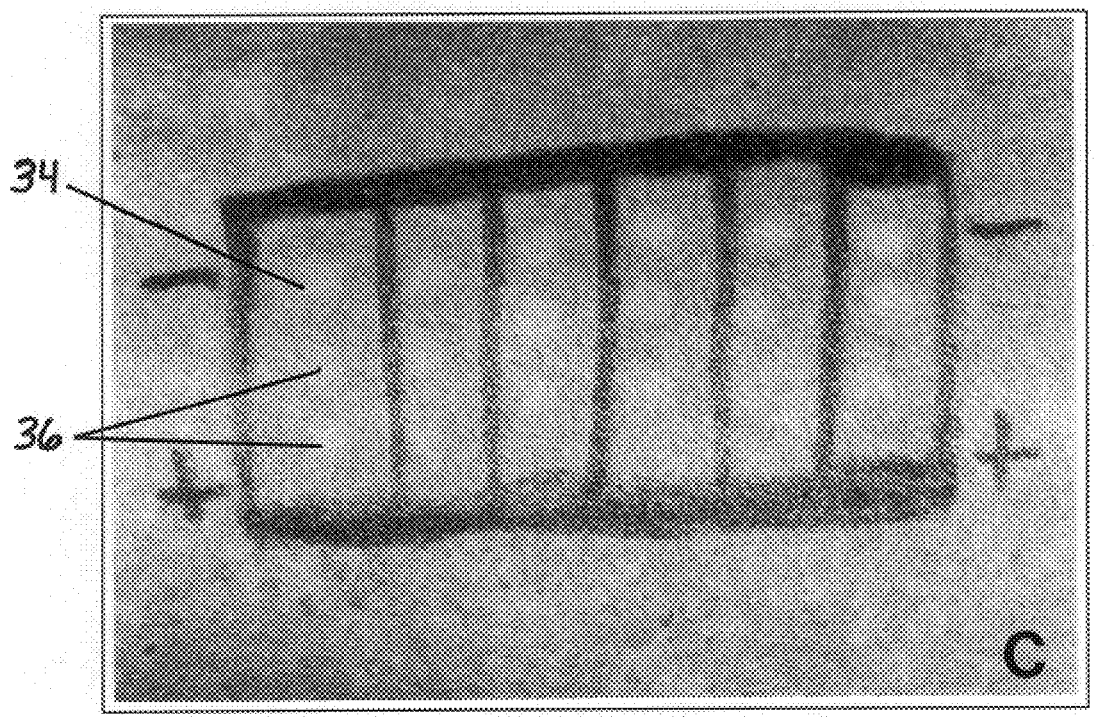
FIG. 6c is a photograph of the test sites of FIGS. 6a and 6b six months after laser exposure.

As shown in FIG. 6c, which is a photograph of the test sites of FIGS. 6a and 6b shown six months after exposure, clinically significant blanching has occurred at uncooled sites 34 and cooled sites 36. Blanching at the cooled sites indicates that selective laser photothermolysis did occur. Such blanching implies an adequate core temperature necessary to destroy the port wine stain blood vessels was achieved with the described laser treatment. These results suggest the cooling following exposure to a short cryogenic spurt of the order of tens of milliseconds is preferentially localized to the epidermis, while the deeper temperature of the port wine stain vessels remain unchanged.

Typically, port wine stain patients undergoing laser therapy with a flashlamp-pumped pulse dye laser report sensations like a "hot pin prick" or a "elastic band snapping against the skin." The discomfort level is energy dependent and increases with high light dosages and also varies with the sensitivity of the treated anatomical site. Pain tolerance generally decreases with decreasing patient age. An additional advantage of dynamic epidermal cooling is reduction and in some cases, elimination of this discomfort. When the epidermis is rapidly cooled with cryogenic spurts longer than 20 milliseconds immediately prior to the laser exposure, the subjects in the present study reported feeling "nothing at all." Subjects treated with a cryogenic spurt as short as 5 milliseconds report significant improvement to the level of comfort associated with flashlamp-pumped pulsed dye laser therapy.

There are two reasons suggested for pain reduction reported by port wine stain patients when using dynamic epidermal cooling prior to laser exposure. First, the maximum surface temperature achieved immediately after laser exposure is lower and in some cases as much as 40 degrees Centigrade lower on the cooled site as compared to the uncooled site. Second, cryogen remaining on the skin evaporates and continues to remove trapped heat through the skin-air interface following laser irradiation. Therefore, the temperature of the post irradiated epidermis decreases more rapidly on the cooled site as compared to the uncooled site.

As stated above, the results of FIGS. 4 and 5 were obtained using an 80 millisecond cryogenic spurt. However, similar surface temperature reductions have been attained using shorter spurts. This suggests that the instantaneous temperature drop, $T_0$, prior to laser exposure is not the only thermal effect responsible for the observed results. Even more important is the rapid removal of heat from the epidermis after pulsed laser exposure due to the establishment of a large temperature gradient near the skin surface.

The heat loss from human skin in contact with air is insignificant because air is an excellent thermal insulator. With no cooling, heat diffusing away from the absorbing melanin layer and port wine stain blood vessels builds up near the skin surface and produces an elevated surface temperature that persists for quite some time after laser exposure. Eventually, lateral thermal diffusion and cooling by blood perfusion eliminates the heat built up near the surface, but this may take several seconds.

It is believed that an important element in dynamic cooling is removal of heat that builds up near the skin surface by the evaporating cryogenic liquid. Cryogen applied to the skin creates a heat sink below the surface of the skin that can remove heat before, during and after laser exposure. The heat sink persists for as long as the liquid cryogen remains on the skin surface. For any given cryogenic spurt, the size or capacity of the sink is proportional to the area between the corresponding temperature curve shown in FIG. 2 and a horizontal line at ambient skin temperature with approximately 30 degrees Centigrade. This is represented in FIG. 2 as a striped area 38 for a 10 millisecond cryogenic spurt.

One goal then is to create with dynamic cooling a heat sink that can rapidly remove the trapped heat without cooling the port wine stain blood vessels in region 12. An important factor in drawing heat out of the skin is the temperature gradient that is established near the skin surface. The steeper the gradient, the faster a given quantity of heat is withdrawn. Thus, to be successful, the cryogen should produce a large surface temperature drop as quickly as possible. Moreover, the quantity of cryogen delivered can be controlled and thus, residual heat is removed by cryogen that has remained on the skin surface after laser exposure. If additional heat must be removed, more cryogen can be applied immediately after laser exposure. Thus, the present invention contemplates not only a cryogenic spurt immediately prior to laser exposure, but also one or more cryogenic spurts thereafter.

The complexity of the dynamic cooling process warrants a careful choice of the cryogen and optimization of several cooling parameters. According to the invention, the cryogen is selected based upon the following factors. The cryogen must have: (1) sufficient adhesion to maintain good surface contact with the skin; (2) a high thermal conductivity so the epidermis can be cooled very rapidly prior to laser exposure; (3) a low boiling point to establish a large temperature gradient at the surface; (4) a high latent heat of vaporization to sustain evaporative cooling of the epidermis after laser exposure; and (5) no adverse health or environmental effects. Although the illustrated embodiment has described the use of tetrafluoroethane, many other cryogens could be substituted with similar results provided that they had one or more of the above factors in their favor.

Further, according to the invention, selectivity of the dynamic cooling of the epidermis can be optimized by controlling: (1) duration of the cooling spurt or spurts; (2) quantity of cryogen deposited on the skin surface so that the effect of evaporative cooling can be maximized; and (3) timing of dynamic cooling relative to laser exposure.

Further, it is contemplated that application can be maximized using a portable hand piece which incorporates a laser fiber together with a miniature solenoid valve to time release cryogenic spurts onto the skin. In this case, single hand-held unit would be employed replacing solenoid valve 22 and laser delivery hand piece 32 of FIG. 4. The use of a single instrument to provide both directed cryogenic sprays to selectively cool certain areas of the skin relative to the irradiated spot and to provide the laser beam is expressly contemplated.

The importance of dynamic epidermal cooling has broad implications for the development of future laser systems for port wine stain therapy. Currently, only a small proportion of patients are able to realize 100 percent fading of their port wine stains even after undergoing multiple laser treatments. One reason for treatment failure has been the inadequate heat generation within large port wine stain blood vessels. A 450 microsecond pulse duration shown in the illustrated embodiment is too short to generate sufficiently high core temperatures over long enough periods of time to destroy irreversibly large port wine stain blood vessels. An improved therapeutic outcome is expected for laser systems utilizing the present invention with pulse durations of the order of several milliseconds. Although longer pulse durations will certainly destroy larger port wine stain blood vessels, such laser systems will also produce greater epidermal injury due to nonspecific absorption by melanin and heat dissipation from the injured vessels. Thus, it is within the scope of the invention to selectively cool and protect the overlying epidermis during longer pulse exposures.

For example, in addition to repetitive patterns of pulsed cryogenic spurts on the laser site, the present invention contemplates the continuous washing of the laser site before, during and after the laser exposure. The protocol by which the cooling substance is applied to create the heat sink on the epidermis surface is not limited or restricted in the invention as long as the time between the onset of when the cooling of the epidermis occurs and the laser firing is short when compared to the thermal diffusion time of the biological target sought to be thermally destroyed, or in this case, the port wine stain.

Further, although the present invention has been described in the context of port wine stains, it must be specifically understood that the use of dynamic cooling in conjunction with laser surgery can also be directly applied to many different applications in the field of dermatology, such as laser treatment of tattoos, and epidermal and dermal melanoses; in the field of ophthalmology, such as cornea surgery; orthopedics and in the field of dentistry. The methodology and apparatus can be applied in any case where it is important to maintain the temperature or thermal damage to adjacent or overlying tissues at a low level while heating or thermally impacting other target tissues.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the essential idea of the invention.

We claim:
1. An apparatus for laser treatment of biological tissue comprising:

a pulsed laser;

a controllable sprayer for providing a spurt of a cryogen to an irradiation site in direct contact on said biological tissue to provide a controlled amount of said cryogen on said irradiation site according to a predetermined dynamic thermal profile to be established within said biological tissue at said site in which biological tissue in a first superficial region is not substantially injured and in which biological tissue in a second deeper region is thermally mediated; and a timing control for triggering said pulsed laser and controlling said controllable sprayer, said laser being triggered by said timing control to fire a predetermined laser pulse after said controllable sprayer provides said controlled amount of said cryogen on said irradiation site to establish said predetermined dynamic thermal profile within said biological tissue at said site, whereby said irradiation site of said biological tissue is dynamically cooled to selectively allow laser treatment of tissue portions of said irradiation.

2. The apparatus of claim 1, wherein said pulsed laser is a flashlamp-pumped pulsed dye laser.

3. The apparatus of claim 1, wherein said timing control comprises a digital delay generator, a time duration of said spurt of cooling substance being determined by a triggering delay generated by said digital delay generator coupled to said controllable means and to said pulsed laser.

4. An apparatus for laser treatment of biological tissue comprising:

a pulsed laser;

a controllable means for providing a spurt of a cooling substance to an irradiation site on said biological tissue; and a timing control for triggering said pulsed laser and said controllable means for triggering said pulsed laser to fire a predetermined laser pulse after said controllable means provides said spurt of cooling substance, wherein said controllable means comprises a cryogenic reservoir and an electronically controlled solenoid valve coupled to said cryogenic reservoir for adiabatically releasing a spurt of said cryogen over a preselected time period, whereby said irradiation site of said biological tissue is dynamically cooled to selectively allow laser treatment of tissue portions of said irradiation.

5. An apparatus for performing laser treatment of biological tissues comprising:

a cryogenic sprayer adapted to cool a selected portion of said biological tissue for a predetermined first time period to establish a predetermined nonequilibrium dynamic temperature gradient through said tissue so that substantially only said selected portion of said biological tissue is cooled by a predetermined minimum temperature drop, said predetermined dynamic temperature gradient being established by providing a spurt of a predetermined amount of cryogenic liquid in direct contact with said biological tissue for said first time period at a site which is later irradiated for a predetermined second time period;

an energy source for irradiating a superficial and deeper part of said selected portion of said biological tissue for said second time period immediately after said first time period to thermally treat said deeper part of said biological tissue while leaving said superficial part of said biological tissue substantially undamaged, said cryogenic liquid having a latent heat of vaporization, said superficial part of said biological tissue being cooled for said second time period by a change of state of said cryogenic liquid to vapor, heat being quickly dissipated from said superficial part of said biological tissue by means of supplying said latent heat of vaporization to said cryogenic liquid, said heat being dissipated in an amount as determined by said predetermined amount of cryogenic liquid applied to said superficial part of said biological tissue, the amount of dissipation of said heat from said superficial part of said biological tissue being specified by said predetermined amount of said cryogenic liquid applied to said superficial part of said biological tissue and by said latent heat of vaporization of said cryogenic liquid; and a controller coupled to said cryogenic sprayer and said energy source for controlling said cryogenic sprayer and said energy source, whereby said deeper part of said selected portion of said biological tissue may be laser treated without damage to said superficial part.

6. The apparatus of claim 5, wherein said superficial part is adjacent to said deeper part and wherein said energy source has a characteristic wavelength of radiation so that irradiating said deeper part of said biological tissue is performed by irradiating through said superficial part of said biological tissue.

7. The apparatus of claim 6, wherein said biological tissue is skin, said superficial part being epidermis and said deeper part being dermis lying beneath melanin contained in said epidermis and wherein said controller controls said cryogenic sprayer and said energy source to establish a predetermined dynamic temperature profile that is dynamically cooled substantially only in said epidermis.

8. The apparatus of claim 5, wherein said cryogenic sprayer disposes cryogenic droplets at said site.

9. The apparatus of claim 5, wherein said cryogenic sprayer disposes a cryogenic mist at said site.

10. The apparatus of claim 5, wherein said controller controls said cryogenic sprayer to establish a thermal heat sink thermally coupled to said superficial part of said biological tissue.

11. The apparatus of claim 10, where said controller controls said cryogenic sprayer to substantially eliminate an air-to-surface insulating barrier at said superficial part of said biological tissue.

12. The apparatus of claim 5, wherein said controller controls said cryogenic sprayer to provide said cryogenic spurt to said superficial part of said biological tissue by disposing a liquid at a predetermined cooled temperature onto the surface of said superficial part of said biological tissue, said liquid having a boiling point below normal temperatures of said superficial part of said biological tissue and wherein said first predetermined time period of said cryogenic spurt has a time duration sufficient to provide approximately a 40–50 degree Centigrade temperature drop at said surface of said superficial part of said biological tissue.

13. The apparatus of claim 12, wherein said time duration of said cryogenic spurt is of the order of tens of milliseconds.

14. The apparatus of claim 5, wherein said controller controls said cryogenic sprayer and energy source to reestablish a predetermined dynamic temperature profile in said superficial part of said biological tissue after irradiation of said deeper part of said biological tissue, said superficial and deeper parts of said biological tissue being thermally coupled.

15. The apparatus of claim 14, wherein said controller controls said cryogenic sprayer and energy source to reestablish said predetermined dynamic temperature profile in said superficial part of said biological tissue immediately after both said superficial and deeper parts of said biological tissue are irradiated by applying more cryogen to said superficial part immediately after laser irradiation thereof.

16. An apparatus of laser treating port wine stain birthmarks in human skin having an epidermis containing melanin and a dermis containing said port wine stains comprising:

a cryogenic sprayer for dynamically cooling said epidermis by directly applying a controlled amount of a cryogenic liquid to said epidermis such that onset of a predetermined nonequilibrium temperature profile within said epidermis is achieved within a first time period substantially shorter than the thermal diffusion time between said port wine stain in said dermis and said overlying epidermis; and an energy source for immediately thereafter irradiating said port wine stain in said dermis through said epidermis for a second predetermined time period sufficient in length to selectively destroy cutaneous blood vessels within said port wine stain, but for a time duration less than said thermal diffusion time between said epidermis and dermis; and a controller coupled to said cryogenic sprayer and said energy source for controlling said cryogenic sprayer and said energy source so that said epidermis is rapidly cooled by vaporizing said cryogenic liquid simultaneously with irradiating said epidermis, said controlled amount of said cryogenic liquid applied to said epidermis being controlled by offsetting a rate of cooling of said epidermis by vaporization of said cryogenic liquid against a rate of heating of said epidermis by irradiation by said energy source, whereby said port wine stain is destroyed without substantial biological damage to said epidermis.

17. The apparatus of claim 16, wherein said controller controls said cryogenic sprayer and energy source to dynamically cool said epidermis by subjecting said epidermis to a spurt of cryogen to establish a predetermined nonequilibrium temperature profile on said epidermis within said first predetermined time period.

18. The apparatus of claim 17, wherein said first predetermined time period is of the order of tens of milliseconds.

19. The apparatus of claim 18, wherein said controller controls said cryogenic sprayer and energy source to dynamically cool said epidermis by subjecting said epidermis to a spurt of cryogen in an amount sufficient to establish a skin surface temperature of at least approximately 40 degrees Centigrade below normal skin temperature at the end of said first predetermined time period.

20. An apparatus for performing laser treatment of biological tissues comprising:

a cryogenic sprayer to cool a first part of said biological tissue for a predetermined first time period by direct contact of a liquid cryogen to said first part to establish a predetermined nonequilibrium dynamic temperature gradient through said tissue so that substantially only said selected portion of said biological tissue is cooled by a predetermined minimum temperature drop, said predetermined dynamic temperature gradient being defined in said biological tissue for said first time period at a site which is later irradiated for a predetermined second time period;

an energy source for immediately after said first time period irradiating said first part and a second part of said biological tissue for said second time period to thermally treat said second part of said biological tissue while leaving said first part of said biological tissue substantially undamaged; and a controller coupled to said cryogenic sprayer and said energy source for controlling cooling said first part of said biological tissue for said second time period during irradiation by quickly dissipating heat from said first part of said biological tissue through a thin layer of said liquid cryogen on said first part of said biological tissue at a rate high enough to prevent thermal-induced biological damage to said first part of said biological tissue, and for quickly terminating said step of cooling to prevent any substantial removal of heat from said second part of said biological tissue which would interfere with a thermal biological effect to said second part of said biological tissue, whereby said second part of said selected portion of said biological tissue may be laser treated without damage to said first part.

21. An apparatus for performing laser treatment of biological tissues comprising:

a cryogenic sprayer for applying a selected amount of cooling cryogenic liquid in direct contact with a selected proximate portion of said biological tissue for a selected first time period having a beginning and an end;

a laser for irradiating said proximate portion and targeted chromophores in a selected adjacent and distal portion of said biological tissue by a laser beam beginning from said end of said selected first time period and continuing through a selected second time period having a beginning and an end, a controller coupled to said cryogenic sprayer and said laser, said end of said selected first time period being controllable by said controller within a few milliseconds, and wherein said first time period is less than that required to substantially cool said targeted chromophores, and wherein said controller ends irradiation of said proximate and distal portion of said biological tissue at said end of said selected second time period, said end of said selected second time period being controllable within a few milliseconds, and wherein said second time period is less than that at which damage begins to occur in said proximate portion, whereby said distal portion of said biological tissue is thermally surgically mediated without damage to said proximate portion.

22. The apparatus of claim 21, wherein said first time period is selected by said controller according to thermal dosage provided to said proximate portion of said biological tissue during said second time period, which first time period is adjusted according to individual patient characteristics affecting said thermal dosage to said proximate portion during said second time period, and wherein said second time period is selected to provide a thermal dosage to said targeted chromophores of said distal portion of said biological tissue, which thermal dosage is effective to surgically mediate said targeted chromophores.

23. The apparatus of claim 21, wherein said cryogenic liquid is applied by said cryogenic sprayer to said biological tissue in liquid form by fine droplet spraying.

24. The apparatus of claim 21, wherein said controller includes means for applying, irradiating, and ending irradiation are selectively repetitively performed subject to control of said controller according to patient characteristics with a repetition rate controllable within a few milliseconds.

* * * * *

UNITED STATES PATENT AND TRADEMARK OFFICE
CERTIFICATE OF CORRECTION

PATENT NO. : 6,171,301
DATED : November 3, 1997
INVENTOR(S) : Nelson et. al.

Page 1 of 1

It is certified that error appears in the above-identified patent and that said Letters Patent is hereby corrected as shown below:

Column 10, Line 51; column 11, line 27; column 12, line 10; column 12, line 11; column 12, line 58, and column 13, line 25, delete "laser".

Signed and Sealed this

Fifth Day of June, 2001

*Attest:*

*Attesting Officer*

NICHOLAS P. GODICI

*Acting Director of the United States Patent and Trademark Office*